(12) United States Patent
Choi et al.

(10) Patent No.: US 9,937,121 B2
(45) Date of Patent: Apr. 10, 2018

(54) HYDROPHILIC EXTERNAL GEL FORMULATION CAPABLE OF ENHANCING SKIN PERMEABILITY OF TACROLIMUS

(71) Applicant: CHUNG-ANG UNIVERSITY INDUSTRY-ACADEMIC COOPERATION FOUNDATION, Seoul (KR)

(72) Inventors: Young Wook Choi, Seoul (KR); Sang Gon Lee, Seoul (KR); Jongbu Kang, Seoul (KR)

(73) Assignee: CHUNG-ANG UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 15/536,775

(22) PCT Filed: Oct. 28, 2015

(86) PCT No.: PCT/KR2015/011444
§ 371 (c)(1),
(2) Date: Jun. 16, 2017

(87) PCT Pub. No.: WO2016/108413
PCT Pub. Date: Jul. 7, 2016

(65) Prior Publication Data
US 2017/0340558 A1    Nov. 30, 2017

(30) Foreign Application Priority Data
Dec. 30, 2014  (KR) .................. 10-2014-0193899

(51) Int. Cl.
| | |
|---|---|
| A61K 39/385 | (2006.01) |
| A61K 8/02 | (2006.01) |
| A61K 31/44 | (2006.01) |
| A61K 31/70 | (2006.01) |
| A61K 9/00 | (2006.01) |
| A61K 47/14 | (2017.01) |
| A61M 37/00 | (2006.01) |

(52) U.S. Cl.
CPC ............ *A61K 9/0014* (2013.01); *A61K 47/14* (2013.01); *A61M 2037/0007* (2013.01)

(58) Field of Classification Search
None
See application file for complete search history.

(56) References Cited

U.S. PATENT DOCUMENTS

| | | | |
|---|---|---|---|
| 2005/0250804 A1 | 11/2005 | Kannan et al. | |
| 2010/0055138 A1* | 3/2010 | Margulies | A61K 8/02 |
| | | | 424/401 |
| 2013/0116271 A1 | 5/2013 | Ihara et al. | |

FOREIGN PATENT DOCUMENTS

| | | |
|---|---|---|
| KR | 10-2006-0062734 A | 6/2006 |
| KR | 10-2007-0083272 A | 8/2007 |
| KR | 10-2013-0043174 A | 4/2013 |

OTHER PUBLICATIONS

PubChem Entry CID 8146 for Diethylene Glycol Monoethyl Ether (pdf download); 66 pages; downloaded Nov. 16, 2017.*
Lubrizol Product Specification sheet (pdf download); Issued Jun. 14, 2007; Edition:Sep. 9, 2011; downloaded Nov. 16, 2017.*
US Pharmacopeia NF Monograph for Carbopol 934P; USP29-NF24, p. 3293; downloaded Nov. 16, 2017.*
Tinocare GL Technical Information Document; published Mar. 2011; pdf download; 4 pages; downloaded Nov. 16, 2017.*
Behzad Sharif Makhmal Zadeh et al., "The Effect of Chemical Enhancers on Tacrolimus Permeation through Rat Skin" Journal of Pharmacy Research 5(3):1309-1312 (2012).
Yongjun Wang et al., "Enhanced oral bioavailability of tacrolimus in rats by self-microemulsifying drug delivery systems" Drug Development and Industrial Pharmacy, 2011, 37(10):1225-1230.

* cited by examiner

*Primary Examiner* — Jeffrey T. Palenik
(74) *Attorney, Agent, or Firm* — Riverside Law LLP

(57) ABSTRACT

The present invention relates to a formulation for external application to the skin containing tacrolimus, which is a poorly soluble drug used as a second therapeutic agent for atopic dermatitis and, more specifically, to a composition of a hydrophilic external gel formulation capable of enhancing skin permeability of tacrolimus, and a preparation method therefor. The hydrophilic external gel formulation loaded with tacrolimus of the present invention is in an easily preparable practical form with excellent moisturizing performance, and is excellent in spreadability and has improved drug delivery, skin permeability and skin residual capacity when applied to the skin, compared to conventional ointments, and thus can be usefully used for the treatment of atopic dermatitis and other immune diseases.

4 Claims, 12 Drawing Sheets

FIG. 5

| Kinetic models | | Ref. | P1 | P2 | P3 | P4 | P5 | P6 | C1 | C2 |
|---|---|---|---|---|---|---|---|---|---|---|
| Zero-order | $R^2$ | 0.7719 | 0.3562 | 0.3742 | 0.3997 | 0.4381 | 0.4851 | 0.3870 | 0.9854 | 0.7981 |
| | $K_0$ | 0.0681 | 2.514 | 2.821 | 2.920 | 3.273 | 3.664 | 2.881 | 1.0995 | 0.1967 |
| First-order | $R^2$ | 0.5231 | 0.2295 | 0.2348 | 0.2178 | 0.2769 | 0.3403 | 0.2547 | 0.6660 | 0.4467 |
| | $K_1$ | 0.0125 | 0.0181 | 0.0195 | 0.0235 | 0.0207 | 0.0378 | 0.0185 | 0.0538 | 0.0229 |
| Higuchi | $R^2$ | 0.8000 | 0.6071 | 0.6459 | 0.6847 | 0.7083 | 0.6459 | 0.6480 | 0.9789 | 0.8802 |
| | $K_H$ | 0.3539 | 7.847 | 10.896 | 11.071 | 12.234 | 10.896 | 7.9542 | 3.2546 | 0.6319 |
| Weibull | $R^2$ | 0.6180 | 0.9399 | 0.9505 | 0.9704 | 0.9521 | 0.9109 | 0.9436 | 0.8147 | 0.8670 |
| | b | 0.3037 | 0.4061 | 0.5517 | 0.641 | 0.6017 | 0.4999 | 0.4113 | 0.8367 | 0.4585 |

$K_0$: Zero-order rate constant
$K_1$: First-order rate constant
$K_H$: Higuchi's equation rate constant
b: Weibull shape factor
$R^2$: Correlation coefficient

HYDROPHILIC EXTERNAL GEL FORMULATION CAPABLE OF ENHANCING SKIN PERMEABILITY OF TACROLIMUS

CROSS-REFERENCE TO RELATED APPLICATIONS

This application is the U.S. national phase application filed under 35 U.S.C. § 371 claiming benefit to International Patent Application No. PCT/KR2015/011444, filed on Oct. 28, 2015, which is entitled to priority under to Korea application no. 10-2014-0193899, filed Dec. 30, 2014.

TECHNICAL FIELD

The present invention relates to a formulation for external dermal application of tacrolimus which is a poorly soluble drug used as a secondary therapeutic agent for atopic dermatitis, and more particularly, to a composition of a hydrophilic external gel formulation capable of enhancing the skin permeability of tacrolimus and a method of preparing the same.

BACKGROUND ART

Atopic dermatitis is a chronic allergic inflammatory disease that occurs in the skin, and is characterized by the occurrence of a red rash and severe itching accompanies it when there is inflammation. When the skin is damaged by frequent scratching caused by pruritus, inflammation may worsen, symptoms may persist, and it is often more severe or more incurable even after adulthood due to a fear of side effects of a therapeutic agent. Atopic dermatitis exhibits a prevalence of 10 to 20% (children) and 1 to 3% (adults) in most countries and the number of patients worldwide is expected to increase to about 138 million people by 2022. Atopic dermatitis may be induced by various causes such as genetic factors depending on family history, environmental factors such as allergens, climate, stress and the like, allergic reactions, abnormalities of the skin barrier and the like.

The treatment of atopic dermatitis is classified into general therapy using skin moisturizers, steroid ointments, topical immunomodulators or the like, auxiliary therapy such as a skin infection treatment, prescription of antihistamines or gamma linolenic acid and the like, or selective therapy using phototherapy, systemic steroids, immunosuppressants or the like. In general therapy for patients with atopic dermatitis, a steroid-based formulation for external application was mainly used to suppress an immune reaction for drug treatment. These topical steroids which have been used as an effective therapeutic agent since 1952 are effective in mitigating an inflammatory reaction, but when topical steroids are continuously used, tolerance develops and various side effects such as atrophodermia, telangiectasia, purpura, acne, hypertrichosis, glaucoma, cataracts, pigmentation or the like occur, and thus it is difficult to apply the drug for a long time. In order to compensate for the disadvantages of these steroids, secondary drugs for treating atopic dermatitis were developed. Examples of the secondary drugs for treating atopic dermatitis include nonsteroidal immunosuppressants such as tacrolimus, pimecrolimus or the like. The drugs contribute to treating the symptoms of atopic dermatitis through a mechanism in which a small amount of the drug is applied to the skin to block the production of cytokines in immunocytes in the dermis layer of the skin and thus T cell activation is suppressed to decrease an immune reaction.

Tacrolimus, which is a nonsteroidal anti-inflammatory immunosuppressant, is a drug derived from metabolites of *Streptomyces tsukubaensis*. Tacrolimus has been used for various skin immune diseases related to immune reactions as well as atopic dermatitis, has less tolerance even when repeatedly used unlike steroids, and is applicable to infants or the elderly. Therefore, tacrolimus is suitable as a secondary therapeutic agent that can be applied to atopic dermatitis or other skin immune diseases.

Since tacrolimus belongs to class II of the Biopharmaceutical Classification System (BCS), which is poorly soluble in water and highly permeable, it is difficult to directly include tacrolimus in a hydrophilic gel formulation. In the case of commercial Protopic®, an ointment including tacrolimus is commercially available. However, ointments composed of lipid components exhibit significantly poor skin permeability compared to a cream formulation or gel formulation including a hydrophilic component, and this fact is directly associated with bioavailability. Therefore, a majority of studies indicate that the ointments composed of lipid components had substantially inferior drug delivery to other formulations. Also, when a patient uses it, there is a problem in which a patient feels uncomfortable because it is not washed well with water and gives a sticky feeling. In previous studies, it has been reported that commercial ointments have a significant difference in permeation rate of the drug depending on the individual and are not absorbed into the dermis but remain in the epidermis due to low permeability and, in this case, the immune environment of the epidermis is converted into an environment into which a virus can penetrate, thereby a varicella-zoster virus infection or a polyoma virus infection may be induced. In order to solve these problems, much research has been conducted on the introduction of a lipid carrier to include a poorly soluble drug such as tacrolimus having high fat solubility in a drug delivery system. There have been efforts to introduce a drug to such a lipid carrier and thus make the drug into a gel formulation, which is significantly effective in enhancing the permeability of a drug. However, it is difficult to be practically used because a manufacturing process is complicated, the cost for introducing a lipid is increased and the process therefor is complicated. Therefore, the development of a practical formulation for external application capable of enhancing skin permeability, which reduces disadvantages of an existing tacrolimus-based formulation for external dermal application, is necessary.

DISCLOSURE

Technical Problem

In order to solve the above problems, the present inventors found that, when tacrolimus is dissolved in Transcutol P which is a solubilizer and an enhancer for skin permeability, and then prepared in a hydrophilic gel form, a drug release rate, skin permeability and a residual amount in the skin are improved compared to an existing ointment, thereby completing the present invention.

Accordingly, the present invention is directed to providing a composition of a hydrophilic external gel formulation capable of enhancing the skin permeability of tacrolimus and a method of preparing the same.

However, the technical scope of the present invention is not limited to the aforementioned objects, and other unmentioned objects can be clearly understood by those skilled in the art from the following descriptions.

Technical Solution

In order to solve the above problems, the present invention provides a hydrophilic external gel formulation for enhancing the skin permeability of tacrolimus, which includes tacrolimus and Transcutol P.

In one example of the present invention, the formulation may further include Carbopol 934P, carnosine, urea, Tinocare GL and glycerin.

In another example of the present invention, the formulation may include tacrolimus at 0.1 to 0.5 wt %, Transcutol P at 1 to 20 wt %, Carbopol 934P at 0.5 to 1 wt %, carnosine at 0.5 to 1 wt %, urea at 3 to 10 wt %, Tinocare GL at 10 to 20 wt %, glycerin at 5 to 10 wt % and water as the remainder.

In addition, the present invention provides a method of preparing a hydrophilic external gel formulation for enhancing the skin permeability of tacrolimus, which includes the following steps:

a) heating Transcutol P in which tacrolimus is dissolved and a hydrophilic component independently and mixing them;

b) adding Carbopol 934P and carnosine as polymeric bases to the mixture and performing homogenization; and c) keeping the homogenized substance at room temperature to induce stabilization.

In one example of the present invention, the hydrophilic component may include urea, Tinocare GL and glycerin.

Advantageous Effects

A hydrophilic external gel formulation including tacrolimus according to the present invention has a form that can be easily prepared, has excellent moisturizing capacity, is practical, and exhibits excellent spreadability, improved drug delivery, skin permeability and skin residual capacity when applied to skin compared to existing ointments, and thus can be usefully used to treat atopic dermatitis and other immune diseases.

DESCRIPTION OF DRAWINGS

FIG. 1 is for selecting a composition of a hydrophilic gel formulation having moisturizing capacity.

FIG. 5 shows results illustrating numerical values obtained by calculating kinetic models (zero-order, first-order, and Higuchi and Weibull models) for interpreting drug release patterns of the formulations.

MODES OF THE INVENTION

Figure 1A:
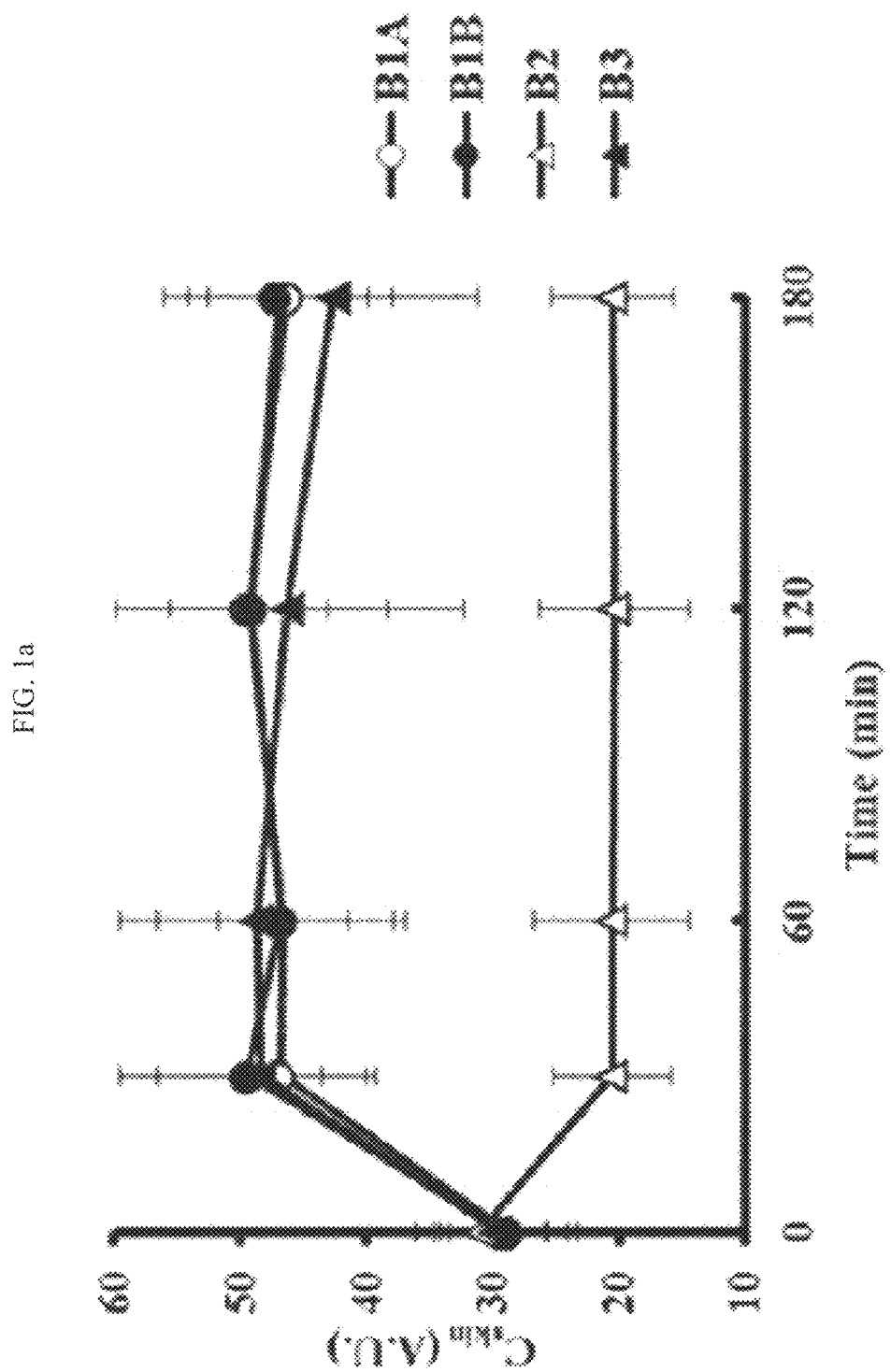
FIG. 1A shows results obtained by measuring moisturizing capacity ($C_{skin}$ (A.U.)) when hydrophilic gel formulations are prepared while varying a composition of a polymeric base and then applied on human skin.

The present invention provides a hydrophilic external gel formulation for enhancing the skin permeability of tacrolimus which includes tacrolimus and Transcutol P, and a method of preparing the same.

The formulation according to the present invention may further include Carbopol 934P, carnosine, urea, Tinocare GL and glycerin, but the present invention is not limited thereto.

The formulation according to the present invention may include tacrolimus at 0.1 to 0.5 wt %, Transcutol P at 1 to 20 wt %, Carbopol 934P at 0.5 to 1 wt %, carnosine at 0.5 to 1 wt %, urea at 3 to 10 wt %, Tinocare GL at 10 to 20 wt %, glycerin at 5 to 10 wt % and water as the remainder, but the present invention is not limited thereto.

A method of preparing a hydrophilic external gel formulation according to the present invention may include the following steps:

a) heating Transcutol P in which tacrolimus is dissolved and a hydrophilic component independently and mixing them;

b) adding Carbopol 934P and carnosine as polymeric bases to the mixture and performing homogenization; and c) keeping the homogenized substance at room temperature to induce stabilization.

The hydrophilic component according to the present invention may include urea, Tinocare GL and glycerin, but the present invention is not limited thereto.

The hydrophilic external gel formulation including tacrolimus according to the present invention was prepared as described in Example 3-1. Transcutol P (2-ethoxyethoxyethanol)), which has high solubility with respect to tacrolimus and can act as an enhancer for skin permeability, was used as a solubilizer of tacrolimus. In order to enhance the moisturizing capacity of the gel formulation, urea which is a natural moisturizing compound, Tinocare GL (or β-1,3-1, 6-glucan) which is a component made of β-glucans constituting the dermis layer of skin, and glycerin which has abilities to improve a moisture supply, moisturizing, skin elasticity and the skin permeation barrier were added. Carbopol 934P and carnosine were used as polymeric bases. Here, Carbopol 934P (or a high molecular weight polymer of acrylic acid crosslinked with allyl ethers of sucrose and pentaerythritol) absorbs and attracts water well, has an ability to form a film, and thus is widely used as a moisturizer. Also, carnosine, which is a biocomponent present in human muscle and brain tissue, is known as a substance having excellent antioxidant activity, and suitably adjusts the pH of a formulation for external application when applied to skin. In addition, in order to identify a function of Transcutol P as an enhancer of skin permeability, enhancers for skin permeability, that is, ethanol, isopropyl alcohol or propylene glycol other than Transcutol P were added in the same proportion to prepare a hydrophilic gel formulation.

It was confirmed that the hydrophilic external gel formulation including tacrolimus according to the present invention contains tacrolimus in almost the same amounts as existing commercial tacrolimus ointments, but exhibited about a 13 to 15 times higher drug release rate, which is even higher than a cream formulation including the same amount of tacrolimus.

In addition, the formulation according to the present invention showed a pattern in which the release rate rapidly increased at an early stage and then gradually decreased, and thus it was confirmed that rapid drug delivery to skin at an early stage is possible (see Example 4).

It was confirmed that the hydrophilic external gel formulation including tacrolimus exhibited about 4 to 9 times higher skin permeability than commercial ointments, had a short lag time when permeating the skin, and exhibited a large final permeated amount. Also, the hydrophilic external gel formulation including tacrolimus exhibited significantly higher skin permeability than a hydrophilic gel formulation and other cream formulations to which Transcutol P was not added (see Example 5).

In addition, a residual amount in the skin was examined after permeation of the drug for 24 hours. As a result, it was confirmed that a 7 to 8 times larger amount of tacrolimus remained in the dermis layer of mouse skin (see Example 6). It was confirmed that the hydrophilic gel formulation exhibited significantly higher skin permeability and a residual amount in the skin than a hydrophilic gel formulation and various cream formulations to which Transcutol P was not added.

In addition, skin irritation was examined 24 hours after the hydrophilic external gel formulation including tacrolimus was applied. As a result, the formulation was confirmed to be a safe form without irritation (see Example 7). Also, the viscosity of the hydrophilic gel formulation was evaluated compared to that of a cream formulation. As a result, it was confirmed that the formulation had excellent applicability when applied to skin because the formulation was initially a semi-solid viscoelastic substance and then flowed when a sufficient force above a certain stress was applied (see Example 8).

Hereinafter, exemplary examples will be described for promoting understanding of the present invention. However, the following examples should be considered in a descriptive sense only, and the scope of the present invention is not limited to the following examples.

EXAMPLES

Example 1. Preparation of Reagent and Material

Tacrolimus (TAC) used in examples of the present invention was obtained from Chong Kun Dang pharmaceutical Corp. Transcutol P (highly purified diethylene glycol monoethyl ether EP/NF; Transcutol® P) used as a solubilizer of tacrolimus was obtained from Gattefosse (Saint Priest, France), and propylene glycol monocaprylate (Capmul™ MCM C8 90) was obtained from ABITEC (Armstrong England). Carbopol 934P used as a polymeric base was purchased from Lubrizol Advanced Materials, Inc. (Cleveland, USA), and carnosine (β-alanyl-L-histidine) was purchased from Tokyo Chemical Industry Co., Ltd. (Toshima, Japan). All other compounds and reagents were purchased from commercially available reagent manufacturers, and secondary distilled water was used in all experiments.

Skin used in the following Examples 5 and 6 was obtained from 5 week-old ICR mice, and the mice were purchased from Orientbio Inc. (Gyeonggi-do, Korea).

Example 2. Selection of Hydrophilic Gel Composition with Moisturizing Capacity

In the case of patients with atopic dermatitis, as the inflammatory reaction is progressed on the skin, erythema and edema occur on the skin, and a recovery process for treatment thereof is repeated. In this case, as a wound is recovered, the outer skin is eliminated and the skin rapidly becomes dry, and thus a decrease in the protective ability of the skin and severe itching are caused. Also, secondary infectious diseases such as infective dermatitis may be induced due to contact during scratching. Therefore, it is very important to avoid irritation and thoroughly moisturize in the treatment of atopic dermatitis. Therefore, experiments for selecting a composition were conducted in Example 2 to prepare a hydrophilic gel formulation having moisturizing capacity.

Each of Carbopol 934P, carnosine, Poloxamer 407 and hydroxyl ethyl cellulose, which are polymeric bases, was selected as a candidate, and in order to identify moisturizing capacity when a hydrophilic gel formulation was prepared using each of the substances, each form was applied on human skin in vivo and then the moisturizing capacity ($C_{skin}$ (A. U.)) of a skin surface was measured through Corneometer CM 820. All experiments were conducted under conditions of constant temperature and humidity on a total of 28 healthy volunteers who had completed consent forms. These experiments were carried out from December to March, and volunteers were washed without the use of other skin care products during the experiments. Compositions of hydrophilic gel formulations whose moisturizing capacities were evaluated are shown in the following Table 1.

TABLE 1

| | Vehicles (w/w) | | | | | |
|---|---|---|---|---|---|---|
| Ingredients | B1A | B1B | B2 | B3 | H1 | H2 |
| Polymeric base | | | | | | |
| Carbopol 934P | 0.5 | 1 | | | 0.5 | 0.5 |
| Carnosine | 0.5 | 1 | | | 0.5 | 0.5 |
| Poloxamer 407 | | | 20 | | | |
| Hydroxyethylcellulose | | | | 4 | | |

TABLE 1-continued

| | Vehicles (w/w) | | | | | |
|---|---|---|---|---|---|---|
| Ingredients | B1A | B1B | B2 | B3 | H1 | H2 |
| Humectants | | | | | | |
| Urea | | | | | 3 | 3 |
| Tinocare GL | | | | | | 10 |
| Glycerin | 5 | 5 | 5 | 5 | 5 | 5 |
| Water | | | q.s. ad 100.0 | | | |

As a result, as shown in FIG. 1A, among four different compositions of B1A, B1B, B2 and B3, B1A and B1B compositions exhibited the highest moisturizing capacity at almost the same level. Although B1A contained a smaller amount of the same components as B1B, B1A and B1B compositions exhibited the same level of effect. Therefore, later experiments were conducted using the B1A composition.

Afterward, changes in the moisturizing capacity of human skin when 3% urea and 10% Tinocare GL, which are hydrophilic substances for increasing moisturizing capacity, were added to the B1A composition, were measured.

Figure 1B:
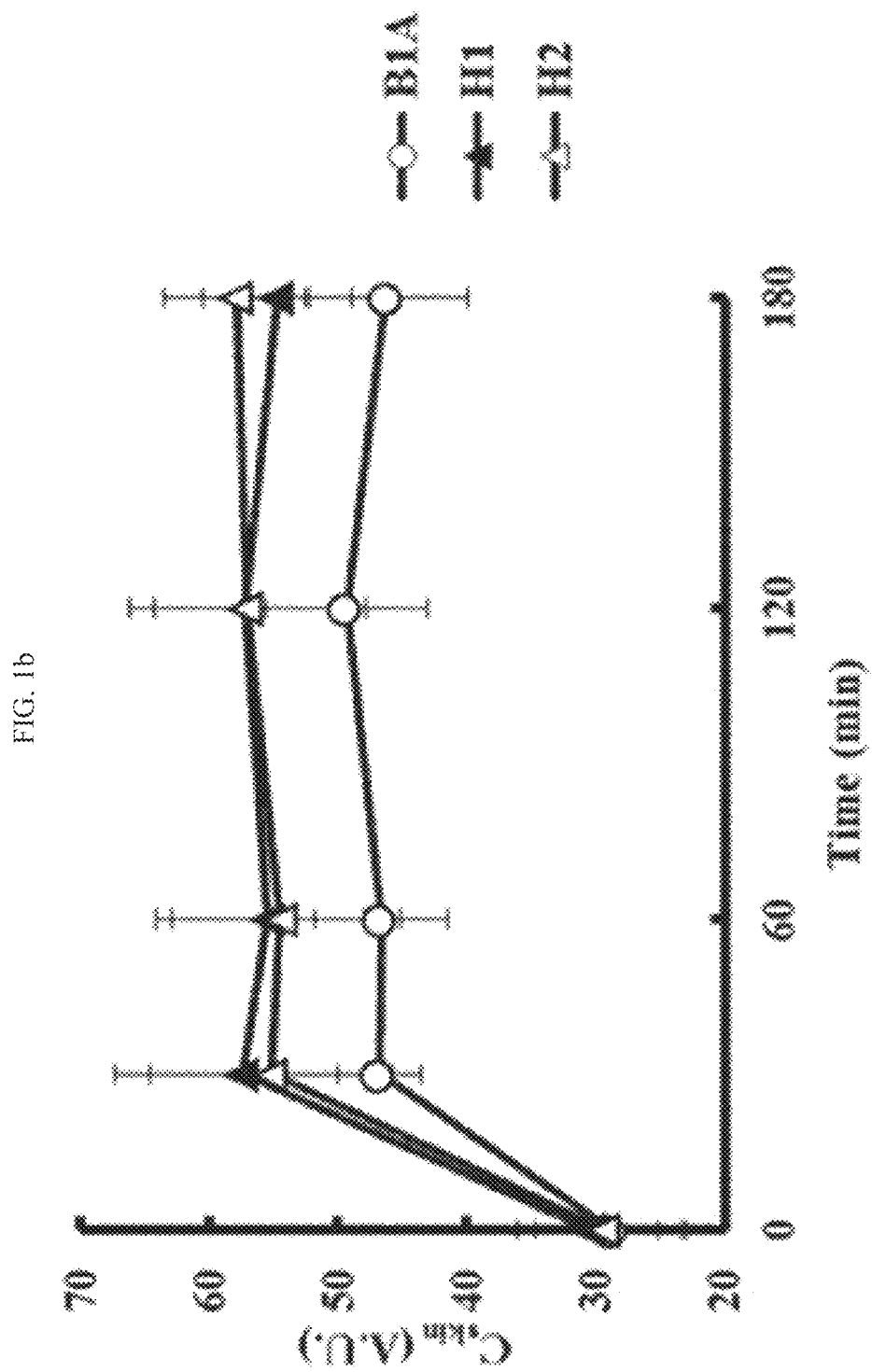
FIG. 1B shows results obtained by measuring moisturizing capacity when hydrophilic gel formulations are prepared while varying a composition of hydrophilic materials in a selected polymeric base and then applied on human skin.

As a result, as shown in FIG. 1B, it was confirmed that moisturizing capacities of the H1 composition in which 3% urea was further added and the H2 composition in which 3% urea and 10% Tinocare GL were further added were higher than that of the B1A composition, and the moisturizing capacity of the H2 composition was maintained better over time.

Example 3. Selection and Preparation of Composition of Gel Formulation Including Tacrolimus Based on the H2 composition selected in Example 2, experiments for selecting a composition of a hydrophilic gel formulation including 0.1 wt % tacrolimus were conducted. In addition, in order to compare it with the gel formulation according to the present invention, a cream formulation including same amount of tacrolimus was prepared to conduct the following experiments. Compositions of hydrophilic gel and cream formulations and processes of preparing the same are shown in the following Examples 3-1 and 3-2. Also, a component in an oil phase which was added upon preparation of each formulation was denoted with (o), and a component in a water phase which was added was denoted with (w) in the following Table 2 in which compositions of hydrophilic gel and cream formulations are described.

3-1. Composition and Preparation of Hydrophilic Gel Formulation

Since tacrolimus is lipid-soluble and a formulation for delivering a drug is in a hydrophilic gel form, a solubilizer that can dissolve tacrolimus and then disperse tacrolimus well was needed. Also, in order to enhance the skin permeability of tacrolimus, Transcutol P was selected as a substance which can act as an enhancer for skin permeability. Transcutol P has a high solubility of 240 mg/g at room temperature with respect to tacrolimus, and it can also be seen that, in a preceding experiment, a gel formulation containing Transcutol P has enhanced permeability compared to a gel formulation containing no Transcutol P. In addition, urea which was added to increase the moisturizing capacity of the gel formulation is known as a natural moisturizing compound, Tinocare GL is a component made of β-glucans constituting the dermis layer of skin, and glycerin is an additive having abilities to improve a moisture supply, moisturizing, skin elasticity and the skin permeation barrier. Carbopol 934P used as a polymeric base absorbs and attracts water well, has an ability to form a film, and thus is widely used as a moisturizer. Carnosine, which is a biocomponent present in human muscle and brain tissue, is known as a substance having excellent antioxidant activity, and appropriately adjusts the pH of a formulation for external application when applied to skin.

The hydrophilic gel formulation including tacrolimus was prepared through the following method. Hydrophilic components except a polymeric base among total components were heated at 80° C., and tacrolimus was dissolved in Transcutol P and heated at the same temperature. Afterward, a hydrophilic component and Transcutol P, in which tacrolimus was dissolved, were mixed through homogenization at a speed of 11,000 rpm for 5 minutes. Next, 0.5 wt % Carbopol 934P was added, homogenization was performed at the same speed for the same time, and then 0.5 wt % Carnosine was added, homogenization was performed again, and then the sample was stabilized at room temperature.

Figure 2:
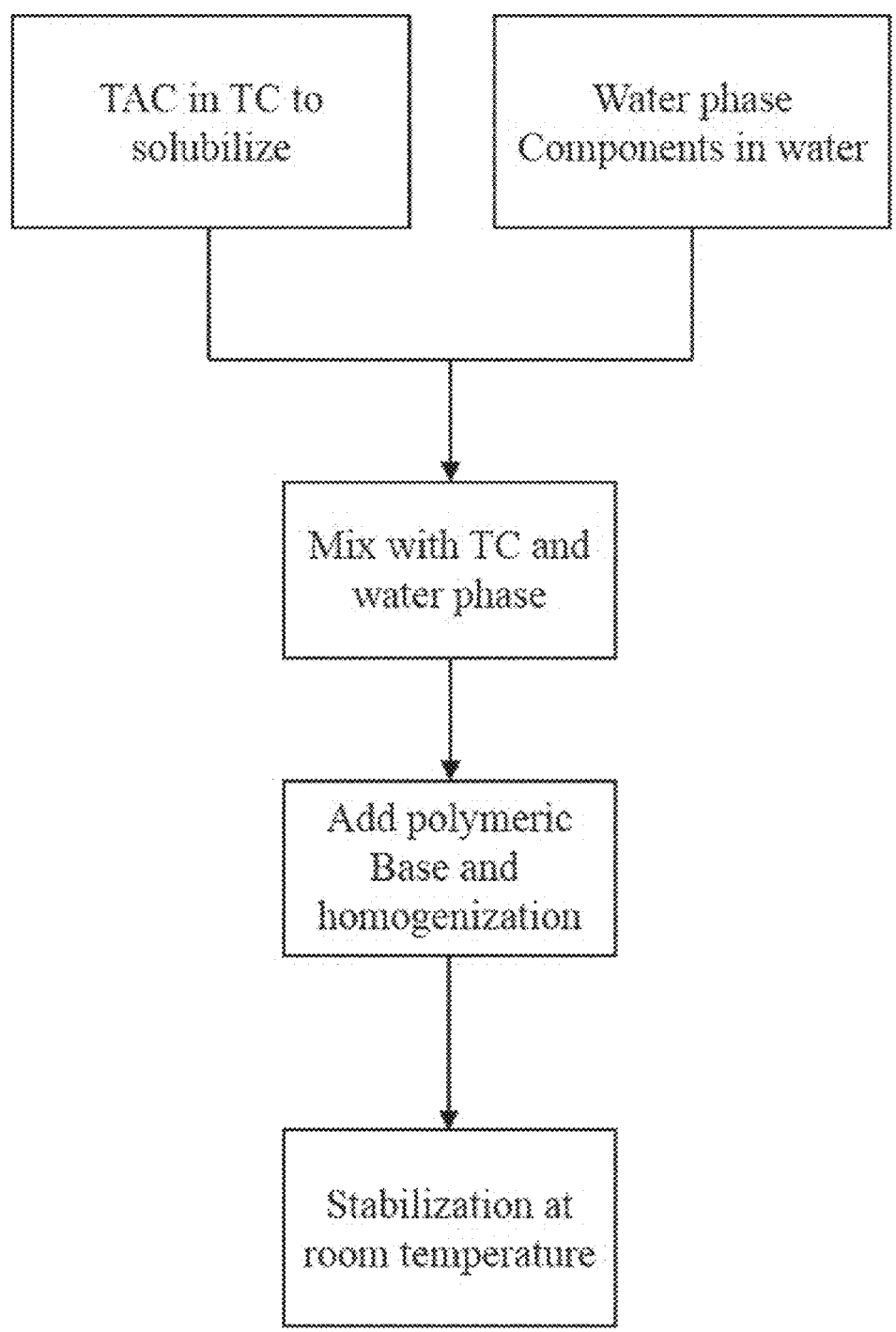
FIG. 2 is a schematic diagram illustrating a process of preparing a hydrophilic gel formulation including tacrolimus.
Figure 3:
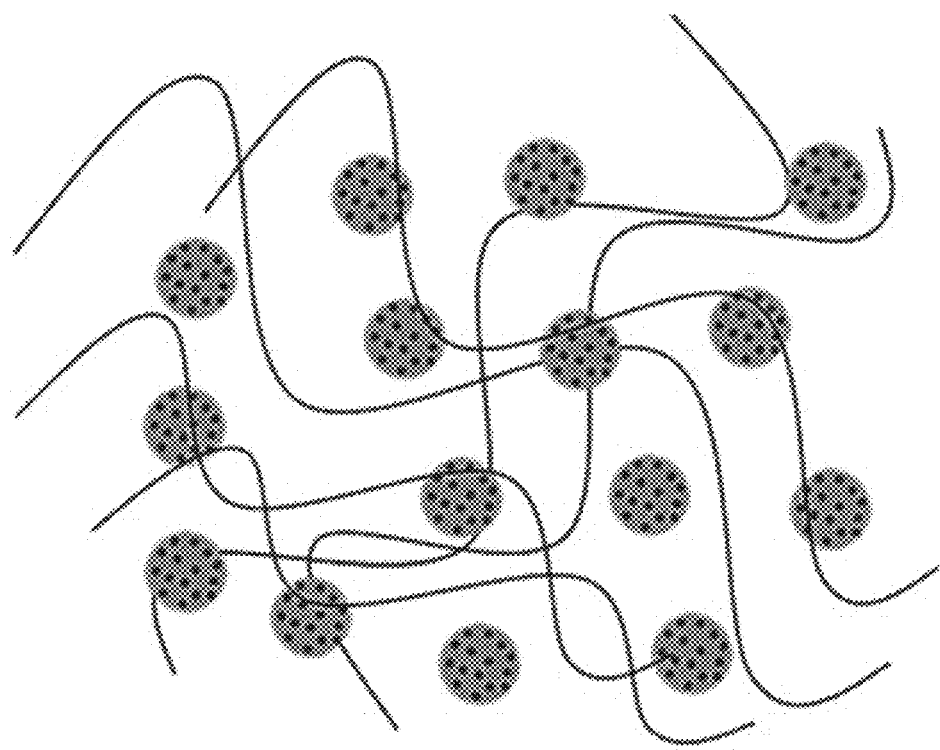
FIG. 3 is a schematic diagram illustrating characteristics of a hydrophilic gel formulation in which oil phase (Transcutol P) particles containing tacrolimus are stably and uniformly dispersed in a carbopol gel matrix.

Detailed compositions of the hydrophilic gel formulation including tacrolimus are shown in the following Table 2. Hydrophilic gel compositions (P1 to P6) were prepared while varying a proportion of Transcutol P in a range of 1 to 20 wt %, and a process of preparing the same is shown in FIG. 2. Also, a schematic diagram of the hydrophilic gel formulation prepared using the method and composition is shown in FIG. 3, which illustrates the characteristics of a hydrophilic gel formulation in which oil phase (Transcutol P) particles containing tacrolimus were stably and uniformly dispersed in a carbopol gel matrix.

In addition, in order to compare the enhancement of skin permeability of Transcutol P that was added as an enhancer for permeability to a hydrophilic gel formulation, ethanol, isopropyl alcohol, or propylene glycol was added at 10 wt % in place of Transcutol P, which is represented by P6, P7, or P8, respectively.

3-2. Composition and Preparation of Cream Formulation

For a cream formulation, forms with improved permeability filed in other patent documents and currently commercialized cream forms were selected, and then modified to have a composition capable of dissolving tacrolimus to prepare a cream form.

Unlike the hydrophilic gel composition of Example 3-1, cream formulations were prepared without the addition of a polymeric base and without the use of Transcutol P as a solubilizer of tacrolimus. Capmul MCM C8 which is an oil phase component was used in place of Transcutol P, and while varying a composition of propylene glycol, liquid paraffin, stearic acid, cetyl alcohol, Tegocare, Olivem 1000 and DL-α-tocopherol acetate as other components, 3 types of a cream formulation were prepared through the following method.

First, a hydrophilic component was heated at 80° C., and tacrolimus was dissolved in Capmul MCM C8 and other oil phase components were added thereto, and heated at the same temperature. Afterward, the hydrophilic component and the oil phase components in which tacrolimus was dissolved were mixed through homogenization at a speed of 11,000 rpm for 5 minutes, and stabilized at room temperature. Detailed compositions are shown in the following Table 2, and C1 to C3 correspond to the compositions of the cream formulations.

TABLE 2

(Unit: w/w %)

| Ingredients | Polymer-based gels | | | | | | | | | Creams | | |
|---|---|---|---|---|---|---|---|---|---|---|---|---|
| | P1 | P2 | P3 | P4 | P5 | P6 | P7 | P8 | P9 | C1 | C2 | C3 |
| Drug | | | | | | | | | | | | |
| TAC (o) | 0.1 | 0.1 | 0.1 | 0.1 | 0.1 | 0.1 | 0.1 | 0.1 | 0.1 | 0.1 | 0.1 | 0.1 |
| Polymeric base | | | | | | | | | | | | |
| Carbopol 934P (w) | 0.5 | 0.5 | 0.5 | 0.5 | 0.5 | 0.5 | 0.5 | 0.5 | 0.5 | | | |
| Carnosine (w) | 0.5 | 0.5 | 0.5 | 0.5 | 0.5 | 0.5 | 0.5 | 0.5 | 0.5 | | | |
| Excipients | | | | | | | | | | | | |
| Urea (w) | 3 | 3 | 3 | 3 | 3 | 3 | 3 | 3 | 3 | 3 | 3 | |
| Tinocare GL (w) | 10 | 10 | 10 | 10 | 10 | 10 | 10 | 10 | 10 | 10 | | |
| Glycerin (w) | 5 | 5 | 5 | 5 | 5 | 5 | 5 | 5 | 5 | 5 | 5 | 10 |
| Transcutol P (o) | 1 | 5 | 8 | 10 | 15 | 20 | | | | | | |
| Ethanol (o) | | | | | | | 10 | | | | | |
| Isopropyl alcohol (o) | | | | | | | | 10 | | | | |
| Propylene glycol (w) | | | | | | | | | 10 | | | 10 |
| Liquid paraffin (o) | | | | | | | | | | | 1.2 | 7 |
| Stearic acid (o) | | | | | | | | | | 2 | | 5 |
| Capmul MCM C8 (o) | | | | | | | | | | 4 | 4 | |
| Cetyl alcohol (o) | | | | | | | | | | 1 | 7 | |
| Tegocare (o) | | | | | | | | | | | 3 | 2 |
| Olivem 1000 (o) | | | | | | | | | | 0.5 | | 3 |
| DL-α-tocopherol acetate (o) | | | | | | | | | | 0.5 | | |
| Water | q.s. ad 100.0 | | | | | | | | | | | |

Example 4. Measurement of Drug Release Rate of Gel Formulation Including Tacrolimus In order to evaluate a drug release rate of the hydrophilic gel formulation including tacrolimus according to the present invention, experiments were performed using commercial ointments and the cream formulations prepared in Example 3-2 and degrees of drug release were compared.

While maintaining conditions of 37° C. and 600 rpm, a modified Franz diffusion cell method using a cellulose nitrate membrane having a pore diameter of 0.1 μm was used. Each formulation was used in an amount of 250 mg, and a drug release rate (%) was analyzed using high-performance liquid chromatography (HPLC) at 210 nm using 0.5 ml of a receptor solvent, which is a 25% ethanol solution, every hour (1, 2, 4, 6, 9, 12, 24 and 48 hr).

Figure 4:
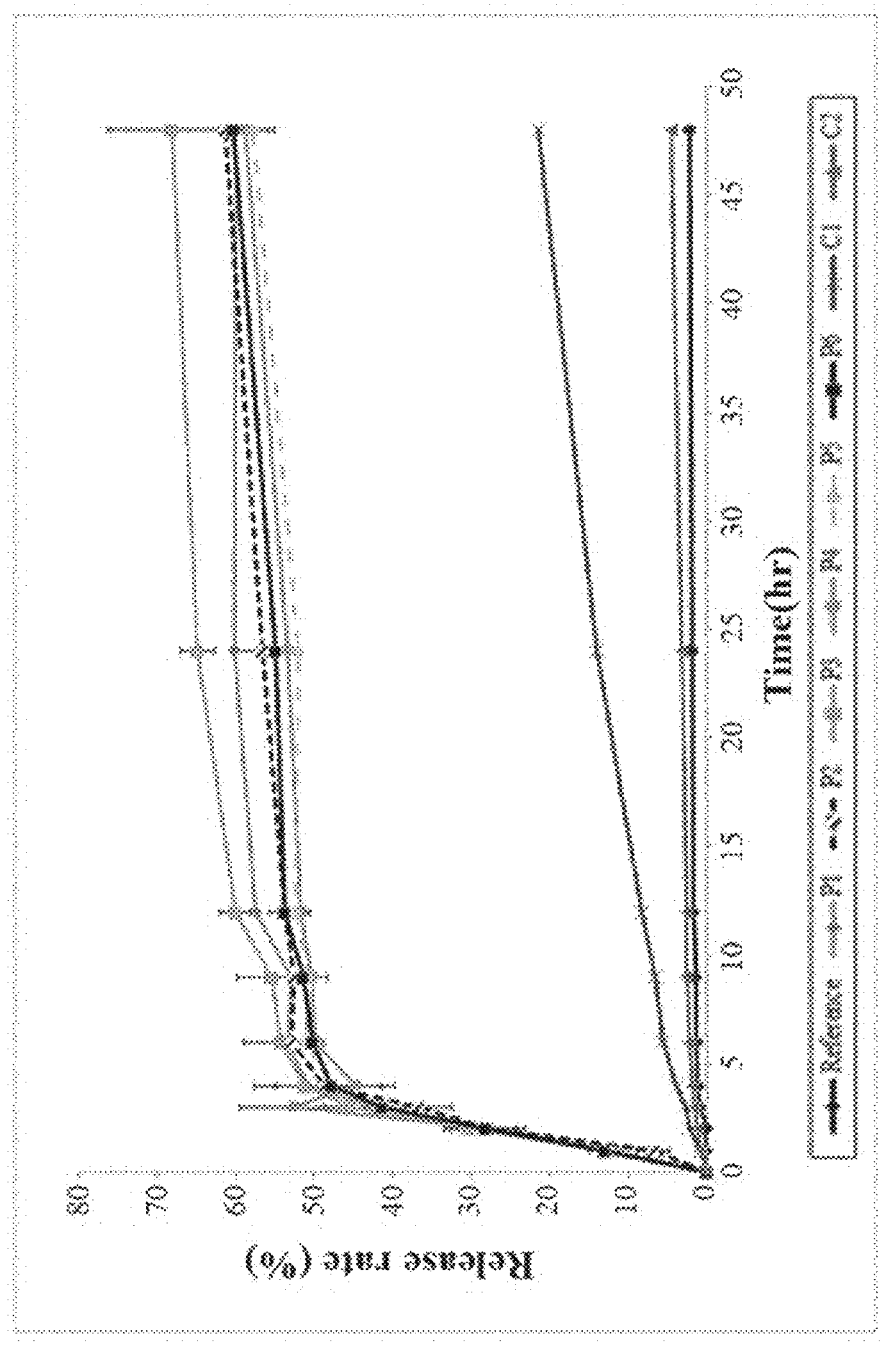
FIG. 4 is a graph illustrating results of a drug release rate (%) of hydrophilic gel/cream formulations including tacrolimus as compared with an existing commercial ointment (Protopic®).

As a result, as shown in FIG. 4, the Transcutol P-added hydrophilic gel formulations (P1 to P6) exhibited a 13 to 15 times higher drug release rate than commercial ointments as references, and there was no significant difference depending on a proportion of Transcutol P. This indicates that Transcutol P acts as a penetration enhancer only on the skin and thus does not act on the membrane in the drug release experiment. Also, it was confirmed that the hydrophilic gel formulations exhibited a significantly higher drug release rate than the cream formulations (C1 and C2).

Kinetic models for interpreting a drug release pattern include zero-order, first-order, and Higuchi and Weibull models. Among these, when a kinetic model was applied, if a correlation coefficient value ($R^2$) was close to 1, the model was determined as the best matching kinetic model Therefore, among these models, the Weibull model with a correlation coefficient value closest to 1 was applied to analyze a drug release pattern of the formulations.

As a result, as shown in FIG. 5, it was confirmed that, in the case of the hydrophilic gel formulation, correlation coefficient values ($R^2$) of P1 to P6 in the Weibull model are 0.9399, 0.9505, 0.9704, 0.9521, 0.9109 and 0.9436, respectively. Also, all values b (shape factor) in the Weibull model are 1 or less, and thus it can be interpreted that the drug release pattern of each gel formulation has a pattern in which the release rate rapidly increases at an early stage and then gradually decreases, and these patterns can also be shown in the graph of FIG. 4. This means that rapid drug delivery is possible for skin drug delivery at an early stage.

Example 5. Measurement of Skin Permeability of Gel Formulation Including Tacrolimus In order to evaluate the skin permeability of tacrolimus using the hydrophilic gel formulation according to the present invention, experiments were conducted through a Franz diffusion cell method as in Example 4. The experiments were conducted using commercial ointments, hydrophilic gel formulations containing enhancers for skin permeability other than Transcutol P and the cream formulations prepared in Example 3-2, and the skin permeabilities thereof were compared with that of the hydrophilic gel formulation according to the present invention.

Hairs in dorsal skin of 5 week-old ICR mice were removed using an electric razor, and the skin was washed with phosphate-buffered saline (PBS) for use. During the experiments, conditions of 37° C. and 600 rpm were maintained, and a 25% ethanol solution diluted with PBS was used as a receptor solvent. Each formulation containing 250 μg of tacrolimus was applied to the skin of a mouse, and then skin permeability over time was quantitatively analyzed using HPLC.

Figure 6:
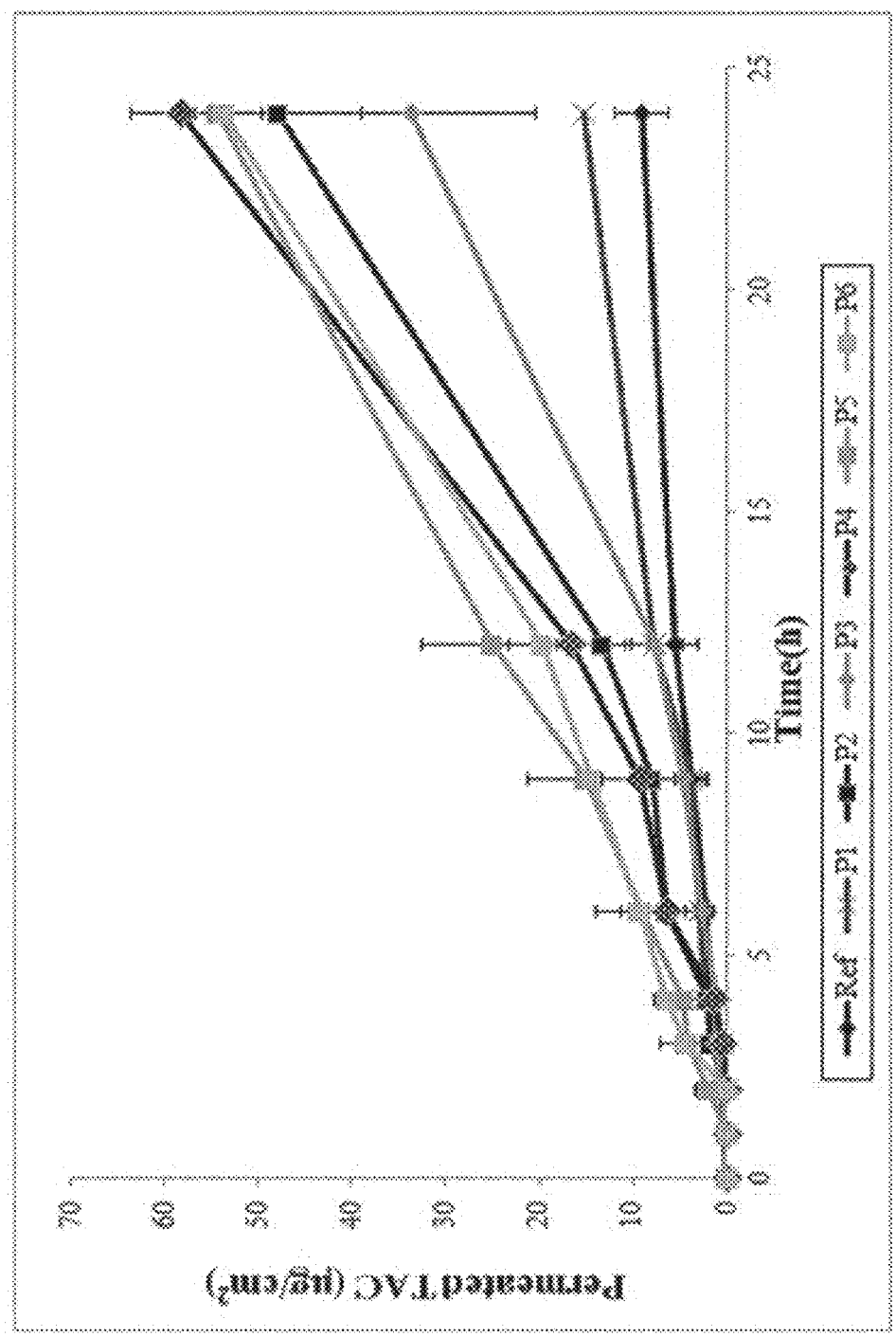
FIG. 6 is a graph illustrating results of a Franz diffusion cell test for measuring the skin permeability of a hydrophilic gel formulation including tacrolimus (TAC) to which Transcutol P in various proportions is added as compared with an existing commercial ointment (Protopic®).

As a result, as shown in FIG. 6, hydrophilic gel formulations containing Transcutol P (P2 to P6) exhibited 4 to 9 times higher skin permeability than commercial ointments as references. When a proportion of Transcutol P was 10 to 20 wt %, the lag time when the drug permeated into the skin was short, and a large amount of the drug finally permeated. That is, as a content of Transcutol P was high, favorable permeability was exhibited. Accordingly, it was confirmed that Transcutol P acts not only as a solubilizer but also as an enhancer for skin permeability.

Figure 7:
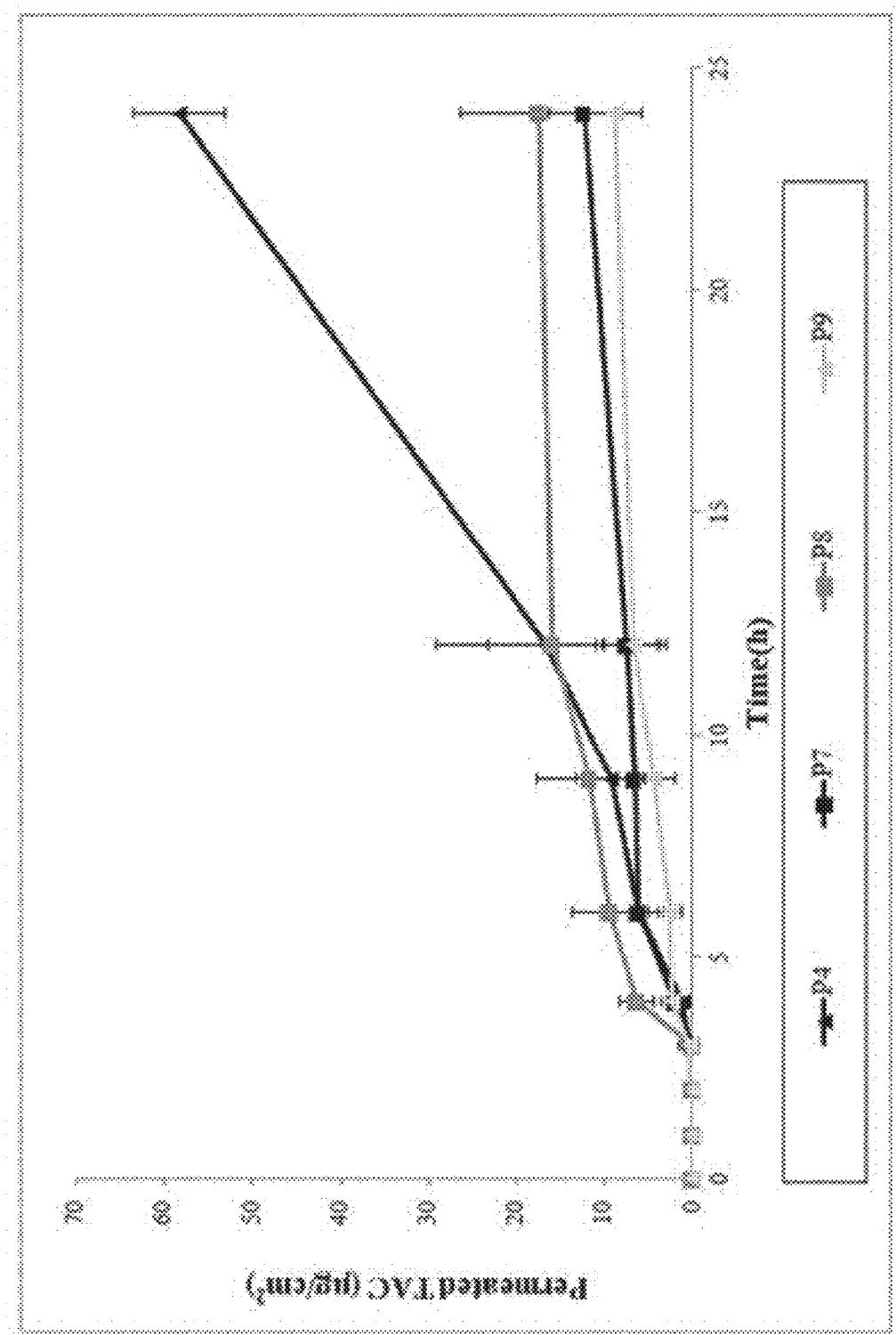
FIG. 7 is a graph illustrating results of a Franz diffusion cell test using a hydrophilic gel formulation to which 10 wt % ethanol, isopropyl alcohol or propylene glycol in place of 10 wt % Transcutol P is added to examine a function of Transcutol P added as an enhancer for skin permeability of tacrolimus (TAC) in a hydrophilic gel formulation.

In addition, as shown in FIG. 7, it was confirmed that the 10 wt % Transcutol P-added formulation (P4) exhibited more excellent skin permeability compared to the hydrophilic gel formulations in which other enhancers for permeability were added (P7 to P9).

Figure 8:
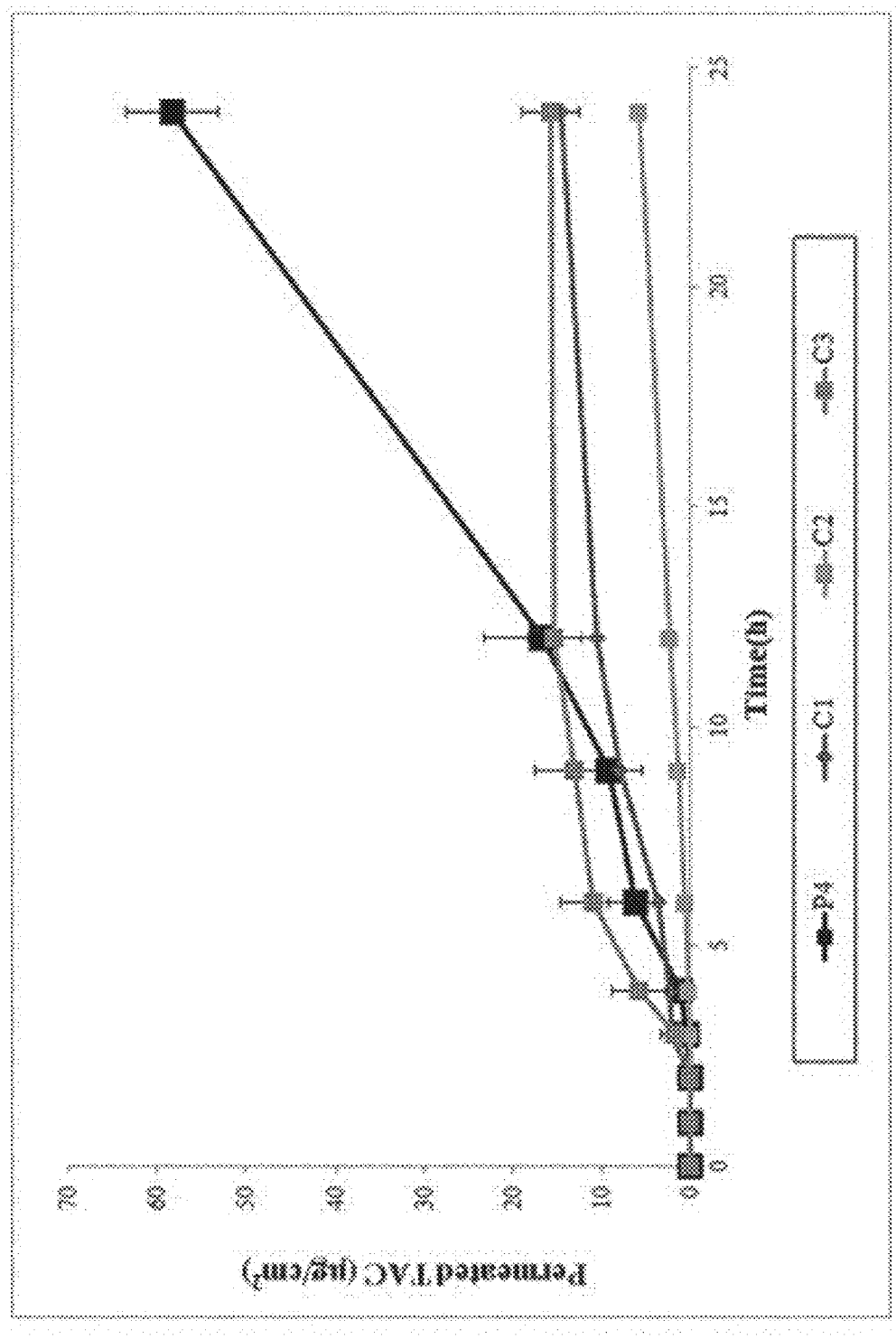
FIG. 8 is a graph illustrating a result of a Franz diffusion cell test for comparing the skin permeability of tacrolimus (TAC) in a hydrophilic gel formulation to which 10 wt % Transcutol P is added and various cream formulations.

Further, in FIG. 8, the 10 wt % Transcutol P-added hydrophilic gel formulation exhibited significantly high skin permeability compared to commercial creams and the cream formulations of other patents (C1 to C3).

Therefore, it was confirmed that Transcutol P significantly affected the enhancement of permeability for transdermal delivery of tacrolimus and the hydrophilic gel formulation exhibited high permeability compared to creams or commercial ointments.

Example 6. Evaluation of Skin Distribution of Gel Formulation Including Tacrolimus The target site of tacrolimus is the dermis layer where an immune reaction occurs when an immune cell mediated inflammatory reaction is induced. Therefore, in addition to the skin permeability of tacrolimus prepared in a hydrophilic gel formulation, it is also important how long tacrolimus remains in the skin after being absorbed into the skin. Therefore, amounts of tacrolimus remaining in the stratum corneum and the dermis layer of skin after permeation of the drug for 24 hours were quantitatively evaluated. Also, as in Example 5, experiments were conducted using commercial ointments, a hydrophilic gel formulation containing enhancers for skin permeability other than Transcutol P, and various cream formulations prepared in Example 3-2.

After murine dorsal skin into which the drug permeated for 24 hours was washed with PBS five times, amounts of tacrolimus remaining in each layer of skin were quantitatively analyzed using HPLC through a tape stripping method for the stratum corneum. Also, the dermis layer was cut into small pieces with scissors, the pieces were homogenized and then subjected to sonication to quantitatively analyze tacrolimus.

Figure 9:
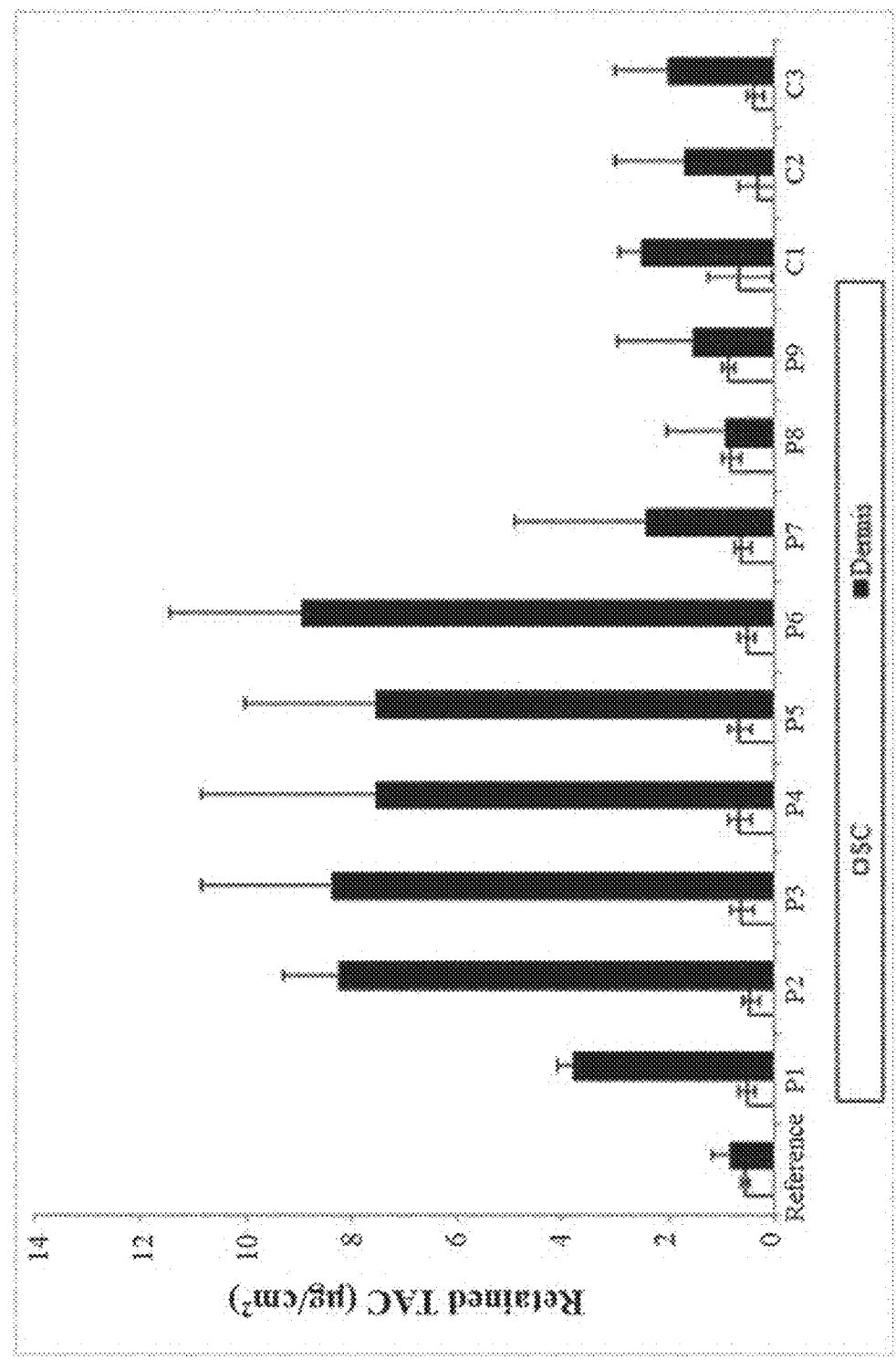
FIG. 9 is a graph illustrating results obtained by quantitatively analyzing amounts of tacrolimus remaining in the stratum corneum and the dermis layer of mouse skin to measure a residual amount of hydrophilic gel/cream formulations including tacrolimus (TAC) in the skin compared to an existing commercial ointment (Protopic®).

As a result, as shown in FIG. 9, there was almost no tacrolimus left in the stratum corneum in the case of all formulations, and there was almost no difference in tacrolimus left in the dermis layer among hydrophilic gel formulations containing enhancers for skin permeability other than Transcutol P (P7, P8 and P9), various cream formulations (C1, C2 and C3), and commercial ointments as references. On the other hand, it was confirmed that a small amount of tacrolimus remained in the case of P1 in which 1 wt % Transcutol P was contained, but 7 to 8 times or more of an amount of tacrolimus remained in the dermis layer compared to commercial ointments in the case of other Transcutol P-added hydrophilic gel formulations, that is, P2 to P6. From the above results, it was confirmed that the skin residual capacity of the gel formulation including tacrolimus is superior to that of existing formulations.

Example 7. Skin Irritation Test of Gel Formulation Loaded with Tacrolimus

In order to evaluate the safety of the gel formulation including tacrolimus, a skin irritation test was conducted for a final formulation including tacrolimus, a final formulation including no tacrolimus, a commercial ointment for comparison (Protopic®). More specifically, a constant amount of the formulation was applied to back of an 8 week old rat and then the applied site was covered with gauze and a band (n=6). 24 hours after application, visual evaluation was conducted through a modified Draize method in which a score of 0 to 4 for edema and erythema was given (0: no change, 1: slight change, 2: moderate change, 3: moderate-severe change, 4: severe change).

Figure 10:
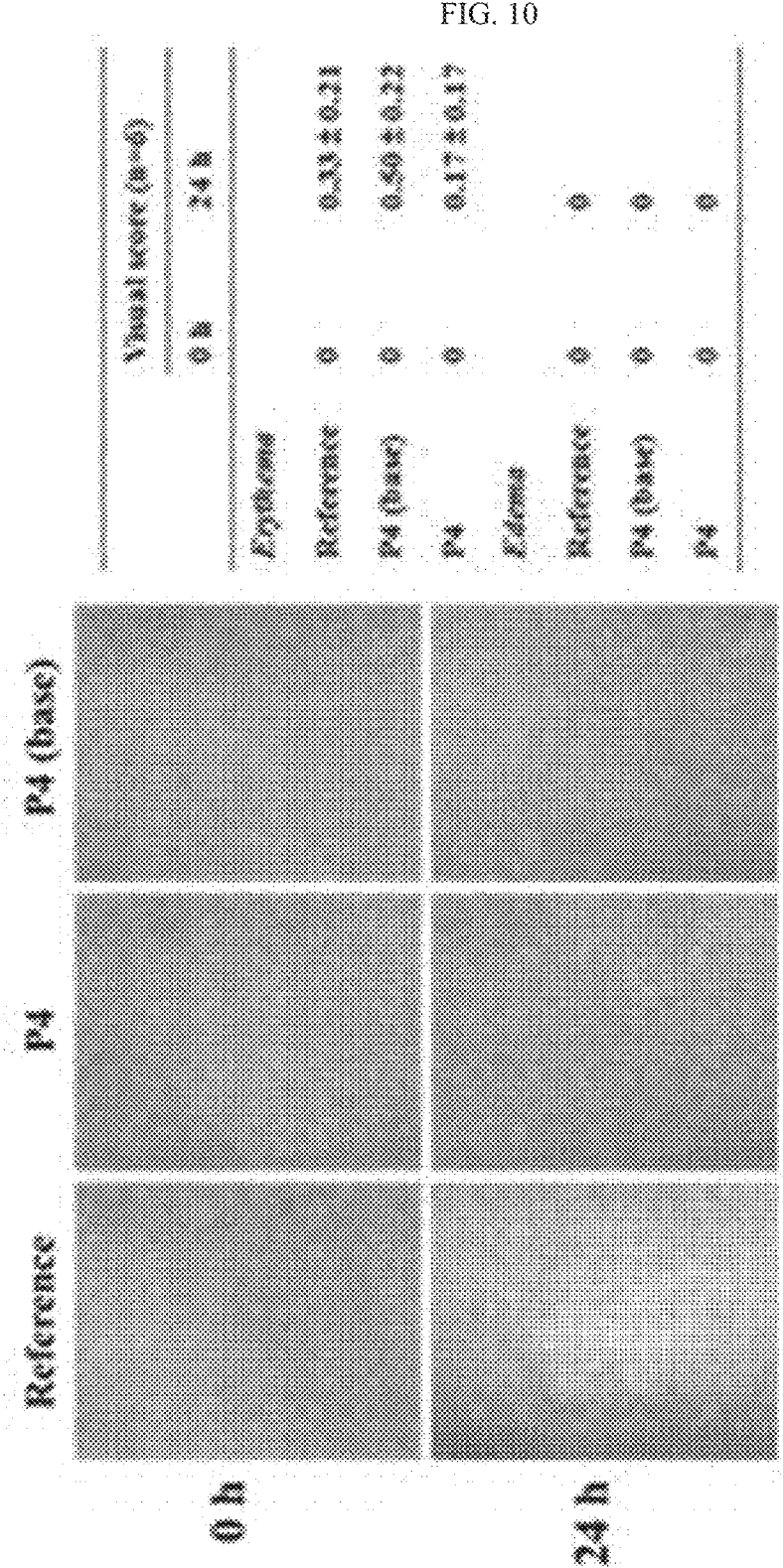
FIG. 10 is an experimental result of evaluating skin irritation after formulations are applied for 24 hours to evaluate the safety of the formulations.

As a result, as shown in FIG. 10, it was confirmed that the final formulation including tacrolimus (P4), the final formulation including no tacrolimus (P4 base) and the commercial ointment for comparison (reference) have an average score of 0.17, 0.5 and 0.33, respectively, indicating that all formulations are in a safe form without irritation.

Example 8. Viscosity Evaluation Test of Gel Formulation Including Tacrolimus

In order to evaluate the viscosity of the hydrophilic gel formulation, the viscosities of hydrophilic gel formulations (P1 to P6) and cream formulations (C1 and C2) were compared. More specifically, after a constant amount of substances was applied, a change in shear stress depending on shear rate was measured using a rheometer.

Figure 11:
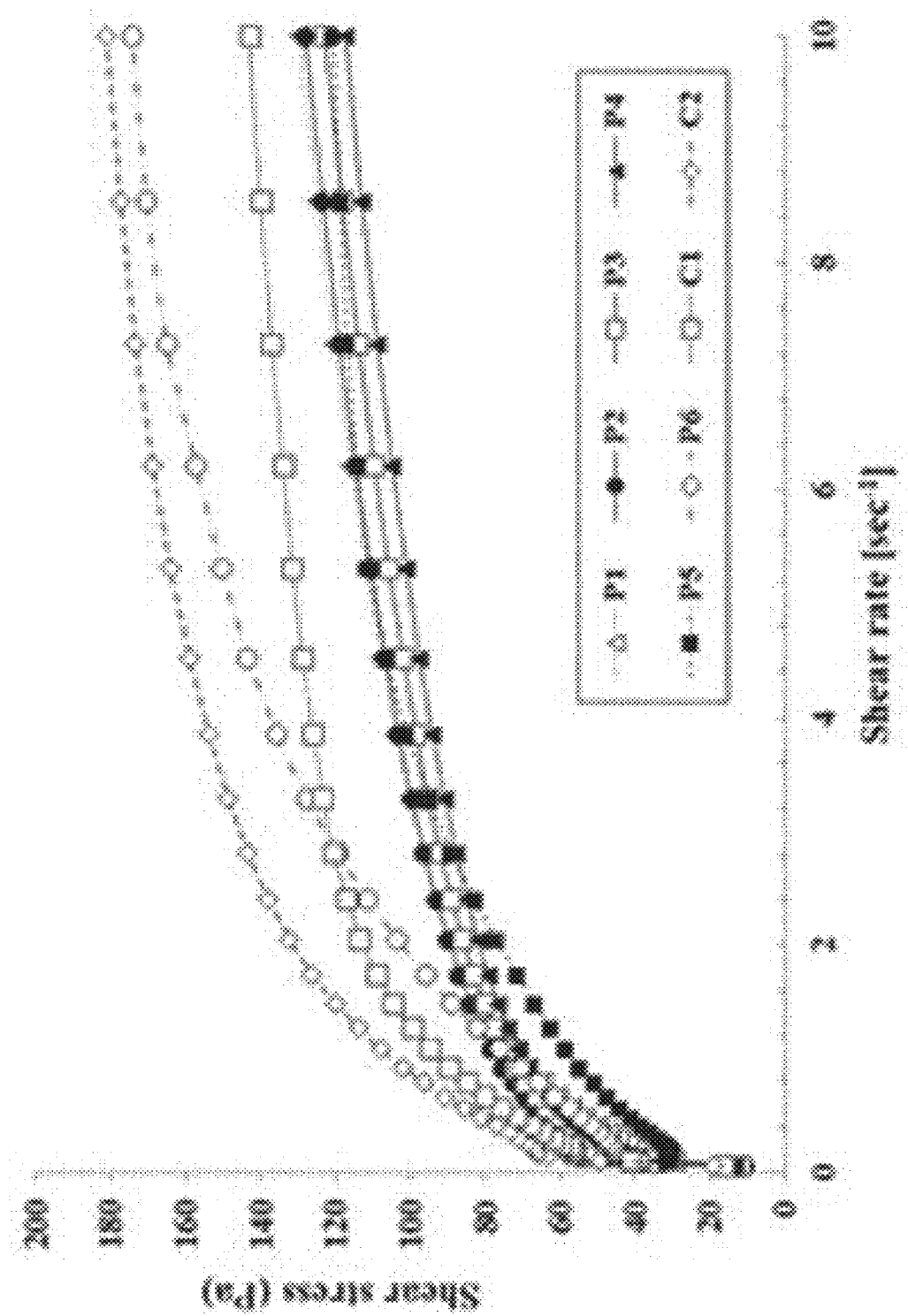
FIG. 11 is a graph illustrating a change in shear stress depending on shear rate in the experiments performed using a rheometer to compare the viscosities of hydrophilic gel and cream formulations.

As a result, as shown in FIG. 11, it was confirmed that hydrophilic gel formulations exhibited appropriate viscosity and a constant pattern of non-Newtonian fluid flow. That is, it was confirmed that the formulations had excellent applicability when applied to skin because the formulations were initially a semi-solid viscoelastic substance and then flowed when a sufficient force above a certain stress was applied.

The above description of the present invention is only exemplary, and it will be understood by those skilled in the art that various modifications can be made without departing from the scope of the present invention and changing essential features. Therefore, the above-described embodiments should be considered as only illustrative in all aspects and not for purposes of limitation.

INDUSTRIAL APPLICABILITY

A hydrophilic external gel formulation including tacrolimus according to the present invention has a form that can be easily prepared, has excellent moisturizing capacity, is practical, and exhibits a significantly improved drug release rate, skin permeability and a residual amount in the skin compared to existing ointments, and thus can be usefully used to treat atopic dermatitis and other immune diseases.

The invention claimed is:

1. A hydrophilic external gel formulation for enhancing the skin permeability of tacrolimus comprising: tacrolimus, 2-(2-ethoxyethoxyethanol), a high molecular weight polymer of acrylic acid crosslinked with allyl ethers of sucrose and pentaerythritol, carnosine, urea, β-1,3-1,6-glucan, and glycerin.

2. The external gel formulation according to claim 1, wherein the formulation comprises: 0.1-0.5 wt % tacrolimus, 1-20 wt % 2-(2-ethoxyethoxyethanol), 0.5-1 wt % of a high molecular weight polymer of acrylic acid crosslinked with allyl ethers of sucrose and pentaerythritol, 0.5-1 wt % carnosine, 3-10 wt % urea, 10-20 wt % β-1,3-1,6-glucan, 5-10 wt % glycerin, and water as the remainder of the formulation.

3. A method of preparing the hydrophilic external gel formulation for enhancing the skin permeability of tacrolimus, according to claim 1, wherein the method comprises the following steps
   a) heating 2-(2-ethoxyethoxyethanol) in which tacrolimus is dissolved and a hydrophilic component independently and mixing them;

b) adding a high molecular weight polymer of acrylic acid crosslinked with allyl ethers of sucrose and pentaerythritol and carnosine as polymeric bases to the mixture and performing homogenization; and
c) keeping the homogenized substance at room temperature to induce stabilization.

4. The method according to claim 3, wherein the hydrophilic component includes urea, β-1,3-1,6-glucan and glycerin.

* * * * *